United States Patent
Koehler et al.

(10) Patent No.: US 10,779,789 B2
(45) Date of Patent: Sep. 22, 2020

(54) EMPIRICAL BEAM HARDENING CORRECTION FOR DIFFERENTIAL PHASE CONTRAST CT

(71) Applicant: KONINKLIJKE PHILIPS N.V., Eindhoven (NL)

(72) Inventors: Thomas Koehler, Hamburg (DE); Bernhard Johannes Brendel, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 142 days.

(21) Appl. No.: 15/031,819

(22) PCT Filed: Oct. 30, 2014

(86) PCT No.: PCT/EP2014/073269
§ 371 (c)(1),
(2) Date: Apr. 25, 2016

(87) PCT Pub. No.: WO2015/067511
PCT Pub. Date: May 14, 2015

(65) Prior Publication Data
US 2016/0242726 A1 Aug. 25, 2016

(30) Foreign Application Priority Data
Nov. 8, 2013 (EP) .................................. 13192149

(51) Int. Cl.
*A61B 6/00* (2006.01)
*A61B 6/03* (2006.01)
(Continued)

(52) U.S. Cl.
CPC ............ *A61B 6/5258* (2013.01); *A61B 6/032* (2013.01); *A61B 6/461* (2013.01); *A61B 6/467* (2013.01);
(Continued)

(58) Field of Classification Search
CPC ......... A61B 6/032; A61B 6/461; A61B 6/467; A61B 6/484; A61B 6/5205; A61B 6/5258;
(Continued)

(56) References Cited

U.S. PATENT DOCUMENTS 4,233,507 A * 11/1980 Volz ....................... A61B 6/032
378/18
5,953,444 A * 9/1999 Joseph .................. G06T 11/005
378/7
(Continued)

FOREIGN PATENT DOCUMENTS

CN 101226642 A 7/2008
JP 2005058649 A 3/2005
(Continued)

OTHER PUBLICATIONS

Chabior et al. "Beam hardening effects in grating based x-ray phase contrast imaging", Medical Physics AP, Metville, NY US, vol. 38, No. 3, Feb. 11, 2011, pp. 1189-1195.*
(Continued)

*Primary Examiner* — David J Makiya
*Assistant Examiner* — Soorena Kefayati
(74) *Attorney, Agent, or Firm* — Larry Liberchuk (57) ABSTRACT

A beam hardening correction method, a related calibration method for tomographic image data and a related apparatus. The tomographic image data includes attenuation data (f) and phase gradient data (g) and/or small angle scattering data (h). A correction value is computed from the attenuation data (f) by applying a function (q) to the attenuation data (f). The correction value is combined (S445) with the phase gradient data (g) or with the small angle scattering data (h).

17 Claims, 5 Drawing Sheets

(51) Int. Cl.
  *G01N 23/046* (2018.01)
  *G01N 23/205* (2018.01)

(52) U.S. Cl.
  CPC ............ *A61B 6/484* (2013.01); *A61B 6/5205* (2013.01); *A61B 6/583* (2013.01); *G01N 23/046* (2013.01); *G01N 23/205* (2013.01)

(58) Field of Classification Search
  CPC .... A61B 6/583; G01N 23/046; G01N 23/205; G06T 11/005
  See application file for complete search history.

(56) References Cited

U.S. PATENT DOCUMENTS

| | | | |
|---|---|---|---|
| 6,324,240 B1* | 11/2001 | Yan | A61B 6/032 378/4 |
| 6,490,476 B1* | 12/2002 | Townsend | A61B 6/032 250/363.03 |
| 6,600,801 B2* | 7/2003 | Raupach | G01N 23/046 378/4 |
| 7,134,787 B2* | 11/2006 | Sun | A61B 6/4035 378/207 |
| 7,453,974 B2 | 11/2008 | Van Steven-Daal | |
| 7,778,381 B2* | 8/2010 | Nishide | A61B 6/032 378/109 |
| 8,023,767 B1* | 9/2011 | Ning | A61B 6/032 382/128 |
| 8,855,395 B2* | 10/2014 | Baturin | A61B 6/484 382/131 |
| 8,873,705 B2* | 10/2014 | Konno | A61B 6/032 378/19 |
| 9,842,414 B2 | 12/2017 | Koehler | |
| 9,934,597 B2* | 4/2018 | Schildkraut | G06T 11/005 |
| 2002/0018540 A1* | 2/2002 | Stierstorfer | A61B 6/032 378/16 |
| 2002/0080912 A1* | 6/2002 | Mackie | A61N 5/1048 340/1.1 |
| 2007/0189444 A1* | 8/2007 | Van Steven-Daal | A61B 6/483 378/6 |
| 2008/0226022 A1* | 9/2008 | Akino | A61B 6/03 378/15 |
| 2011/0103542 A1* | 5/2011 | Allmendinger | A61B 6/507 378/4 |
| 2011/0168878 A1* | 7/2011 | Hoerndler | A61B 6/583 250/252.1 |
| 2011/0235773 A1* | 9/2011 | Baba | A61B 6/4441 378/7 |
| 2013/0026353 A1* | 1/2013 | Yan | A61B 6/032 250/252.1 |
| 2013/0208850 A1* | 8/2013 | Schmitt | G01N 23/20 378/4 |
| 2014/0169653 A1* | 6/2014 | Maack | G06T 5/50 382/132 |
| 2014/0321608 A1* | 10/2014 | Ueki | A61B 6/032 378/18 |
| 2015/0125055 A1* | 5/2015 | Gao | A61B 6/032 382/131 |
| 2015/0131777 A1* | 5/2015 | Makifuchi | A61B 6/463 378/36 |
| 2015/0164456 A1* | 6/2015 | Takamatsu | G06T 11/006 378/4 |
| 2015/0173703 A1* | 6/2015 | Siewerdsen | A61B 6/583 378/20 |
| 2015/0324973 A1* | 11/2015 | Ueki | G01T 1/24 382/132 |
| 2016/0113611 A1* | 4/2016 | Stampanoni | A61B 6/5217 378/36 |
| 2016/0157809 A1* | 6/2016 | Takahashi | A61B 6/542 378/16 |

FOREIGN PATENT DOCUMENTS

| | | |
|---|---|---|
| WO | 2012/029039 | 3/2012 |
| WO | 2013/008712 | 1/2013 |

OTHER PUBLICATIONS

Chabior, et al., "Beam hardening effects in grating based x-ray phase contrast imaging", Medical Physics, AIP, Melville, NY US, vol. 38, No. 3, Feb. 11, 2011, pp. 1189-1195.

Bevins, et al., : "Beam hardening in x-ray differential phase contrast computed tomography", Medical Imaging 2011: Physics of Medical Imaging, SPIE, 1000 20th St. Bellingham WA 98225-6705 USA, vol. 7961, No. 1, Mar. 3, 2011.

Wu, et al., : "An experimental method of determining relative phase-contrast factor for x-ray imaging systems", Medical Physics, AIP, Melville, NY, US, vol. 31, No. 5, May 1, 2004 (May 1, 2004), pp. 997-1002.

\* cited by examiner

EMPIRICAL BEAM HARDENING CORRECTION FOR DIFFERENTIAL PHASE CONTRAST CT

CROSS REFERENCE TO RELATED APPLICATIONS

This application is the U.S. National Phase application under 35 U.S.C. § 371 of International Application No. PCT/EP2014/067511, filed Oct. 30, 2014, published as WO 2015/067511 on May 14, 2015, which claims the benefit of European Patent Application Number 13192149.6 filed Nov. 8, 2013. These applications are hereby incorporated by reference herein.

FIELD OF THE INVENTION

The invention relates to a beam hardening correction method, to a beam hardening calibration method, to an image processor, to a computer program element, and to a computer readable medium.

BACKGROUND OF THE INVENTION

Beam hardening is a source of artifacts in computed tomography CT. Beam hardening is caused by the use of a polychromatic x-ray source and by the fact that the X-ray attenuation depends strongly on energy of the X-ray beam.

In conventional CT, beam hardening leads mainly to cupping and shading artifacts and must be corrected for in order to provide accurate images that are appropriate for diagnostic or other image based reasoning tasks.

Similar artifacts are also present in differential phase contrast imaging (DPCI). In the past, several beam hardening (BH) correction (BHC) algorithms for tomographic differential phase contrast imaging (DPCI) have been proposed for instance in Applicant's WO 2012/029039.

SUMMARY OF THE INVENTION

There may therefore be a need for a different method and related apparatus for beam hardening correction in relation to differential phase contrast image signals and other related image signals.

The object of the present invention is solved by the subject matter of the independent claims where further embodiments are incorporated in the dependent claims. It should be noted that the following described aspect of the invention equally apply to the image processor, to the computer program element and to the computer readable medium.

According to a first aspect of the invention there is provided a beam hardening correction method for tomographic image data acquired by exposure of an object to an x-ray beam emitted by an x-ray source of an imaging apparatus and after passage of the beam through the object. The tomographic image data includes at least attenuation data and at least one of phase gradient data (also referred to herein as "differential data") or small angle scattering data. The method comprises the step of:

combining at least one respective correction value with the phase gradient data or with the small angle scattering data, wherein the respective correction value is computed from the attenuation data (f) by applying a function to the attenuation data. Said combination can take different forms for different embodiments, for instance multiplicative form (in which case the correction value may be referred to as a correction factor) but other combinations such as additive form or otherwise may also be used in some use scenarios.

The image data is in general corrupted by beam hardening which means that the beam's mean energy "grows" as the beam passes through the object. It is proposed herein to "modulate" the phase gradient data g or the small angle scattering data h with the correction factor so that the modulated projection data forms an approximation of an inverse of a beam hardening corruption function. The beam hardening correction function describes the functional relationship between the i) amount of material (in the object) traversed by the beam and ii) the attenuation data given a certain mean energy of the beam. The inverse of the beam hardening corruption function is then the amount of the traversed material, given the attenuation data and the mean energy, and the corrected projection data is an estimate or approximation for the traversed amount of material.

In one embodiment the correction factor is computed only from the attenuation data and not from the phase gradient data or from the small angle scattering data. The correction factor itself is formulated by means of the surrogate function $\hat{q}$ that is thought to approximate the way the mean energy grows as the beam traverses the material. The mean energy growth behavior is thought to be slow and monotonic which is why, in one embodiment, a polynomial is used to model the mean energy growth although other suitable functional models are likewise envisaged herein. The degree of the polynomial is preferably low, that is, the degree is between 2 and 6 but higher degrees such as 7-10 or even higher may also be used.

With the proposed method, neither an explicit knowledge about the x-ray spectrum is required, nor is necessary to know the energy dependence of the detector quantum efficiency or the energy dependence of the efficiency of an interferometer used to acquire the phase gradient data. Although this information can be obtained from experimental and theoretical procedures, the proposed method affords an avenue around these, at times, cumbersome procedures. In other words, the proposed method is "empirical" in that no attempt is made herein to separately account, in the actual algorithmic steps, for all relevant physical causes that have a bearing on the beam hardening effect, but at least the mainly relevant physical causes are thought to be lumped together and captured by said surrogate function. It is also assumed herein, the combined effect of those causes is "slow" enough in the sense that a polynomial can be used as an adequate surrogate.

According to one embodiment, the beam hardening correction method comprises a calibration step wherein the calibration step includes the steps of:

acquiring tomographic calibration image data of a phantom body by using the x-ray source;

determining one or more coefficients $b_k$ of the function by fitting the calibration image data (which is in general beam hardening corrupted) to the known ground truth of the phantom body, wherein the one or more coefficients $b_k$ parameterize said surrogate function $\hat{q}$. The tomographic calibration image date includes at least attenuation data and at least one of phase gradient data or small angle scattering data, each in respect of the phantom body.

In one embodiment the calibration step includes forming (respective) mixed image data from the attenuation data and from either one of the phase gradient data or the small angle scattering data.

The acquisition of the calibration image data may be carried either before or after acquisition of the tomographic image data of the actual object to be imaged. In one aspect, the calibration step is a standalone (method) part of the beam hardening correction method as proposed herein and the calibration step may be carried out in a preliminary phase prior to the above steps in respect of the (tomographic) object image data.

According to one embodiment, the fitting step is based on the least squares method but other curve fitting method such as weighted least squares.

According to one embodiment, the phantom body is formed from a material that incorporates at least one discrete portion having a density different from a density of the surrounding phantom body material.

According to one embodiment, the discrete portion is defined by an air-filled cavity.

According to one embodiment, the imaging apparatus is a computed tomography scanner configured to acquire at least attenuation data and additionally the phase gradient data and/or small angle scattering data.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
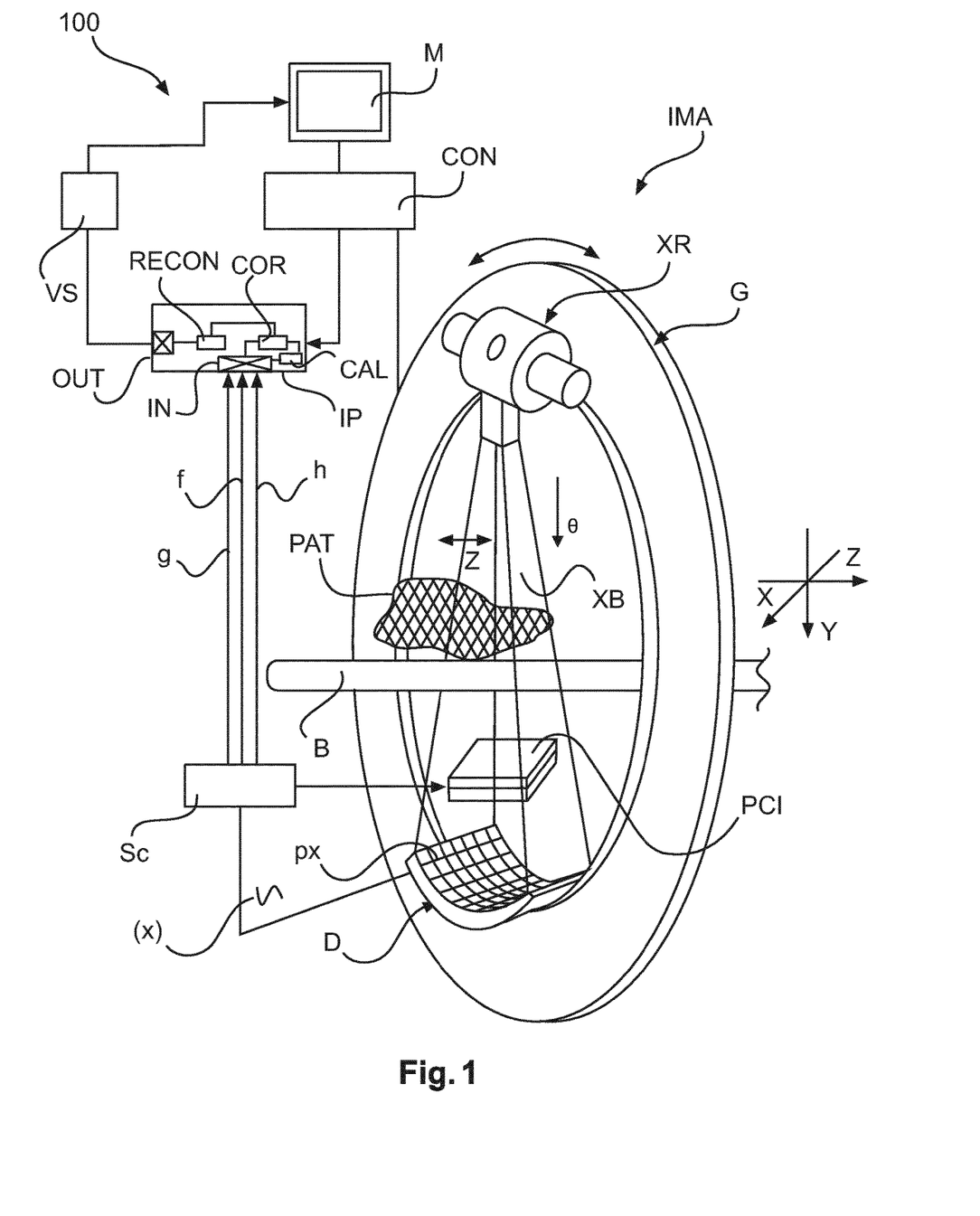
FIG. 1 shows an imaging arrangement.

With reference to FIG. 1, there is shown an imaging system according to one embodiment. Broadly, said imaging arrangement includes an X-ray based CT scanner IMA and a workstation or operating console CON for controlling operation of said scanner IMA.

A general purpose computing system may serve as the operator console CON, and includes an output device such as a display M and an input device such as a keyboard, mouse, and/or the like. Software resident on the console CON allows the operator to control the operation of the system IMA, for example, allowing the operator to select imaging parameters directly or indirectly through selecting a pre-generated imaging protocol. Display unit (such as a monitor/screen) M is communicatively coupled to console CON to aid inputting control information or to view operational states of the scanner or to view images supplied by the scanner or to view images obtained by image processing the so supplied images.

Image rendering of the reconstructed images for display on screen M is by a visualizer VS that is configured to receive image data and visualization information to drive a video card of console CON to so effect display on screen M. Visualization information may include a color value or gray value palette on which the image values are mapped by a mapper to effect display in a desired color value or gray value coding in a desired range.

The scanner IMA includes a stationary gantry and a rotating gantry G, which is rotatably supported by the stationary gantry. The rotating gantry 104 rotates around an examination region, about a longitudinal z-axis. The examination region is formed as an opening or bore in the rotating gantry G.

A subject support B, such as a couch, supports a subject PAT or object PAT to be imaged in the examination region and can be used to position the subject or object with respect to x, y, and/or z axes before, during and/or after scanning. The subject may be human or animal patient and the object may be an item or baggage or other non-living sample. In the following, reference will be made to "object PAT" only for either case.

A radiation source XR, such as an X-ray tube ("tube"), is supported by the rotating gantry 104 and rotates with the rotating gantry G about the examination region, and emits radiation, via a focal spot, that traverses the examination region.

The radiation beam is centered about an iso-center of the bore and defines a generally circular shaped field of view FoV (of the scanner) to reconstruct for a transverse reconstruction plane, whose normal is generally perpendicular to a center ray of the beam and which extends through the iso-center.

A radiation sensitive detector array D (in a suitable housing) is located opposite the radiation source XR, across the examination region. The detector array D includes one or more rows of detector pixels px that detect radiation traversing the examination region and generate an electrical current or voltage signal indicative of the detected radiation. Rotation of rotatable gantry (and thus of at least the X-ray source's focal spot), is effected by one or more controllers and/or one or more drive systems (e.g., a motor, a coupling, etc.).

During an imaging run when the scanner is in use, focal spot rotates over a predetermined angular range on a path (in general an arc or a full circular rotation) around bore B and hence around object PAT therein at a given angular frequency during a scan of at least a part of the object PAT. For each rotation angle θ, the detector detects the radiation emitted by the focal spot after passage through the subject or object at said angle. The radiation experiences attenuation and a certain phase shift of the radiation when considered as a wave rather than a ray during passage through the subject or object. The attenuation is in general proportional to the local densities of the subject or object and the phase shift relates to the real part of the local refractive index of the material. Each detector pixel (opposite focal spot) receives a certain amount of photonic energy and responds by issuing a corresponding electric signal as briefly mentioned above. The collection of said signals is then translated by a data acquisition system DAS (not shown) into a respective digital value. Said value encodes information on the amount of attenuation, phase shift and also the amount of small angle scattering ("dark field") experienced by the x-ray beam. This information (that is, amount of i) attenuation, ii) phase shift and iii) small angle scattering) can be extracted by using an interferometric set-up as will be explained in more detail below at FIG. 2. The collection of the digital values are then consolidated into an array of digital values forming a 1D or 2D X-ray projection image or image raw data for a given acquisition time and projection angle θ. The detector thereby outputs a collection of raw projection images, one or more for each rotation angle θ, to so define a raw image data sinogram. A sinogram is a data structure in which to each projection angle θ there is associated raw image data as detected by the detector D at the respective angle θ). In one embodiment, the detector is of the photon counting type. In an alternative embodiment the detector is of the energy integrating type.

There is also an image processing module IP that is in one embodiment communicatively coupled to console CON to effect image processing. Broadly, image processor IP includes input IN and output OUT interfaces and includes an image reconstruction module RECON that affords an image reconstruction functionality. There is also a correction module COR that operates to correct image data as detected by detector D, Operation of corrector module COR will be explained in more detail below at FIG. 5.

As further shown in FIG. 1, the imaging scanner CT includes phase contrast imaging equipment PCI which allows extracting phase shift gradients from the recorded projection images. This is because, as briefly mentioned, on top of the attenuation suffered by the X-ray in its passage through matter PAT, there is also a phase shift φ, caused by passing material in object PAT.

The basic components of the phase contrast imaging equipment PCI, essentially a grating based interferometer, are briefly described with reference to FIG. 2.

Figure 2:
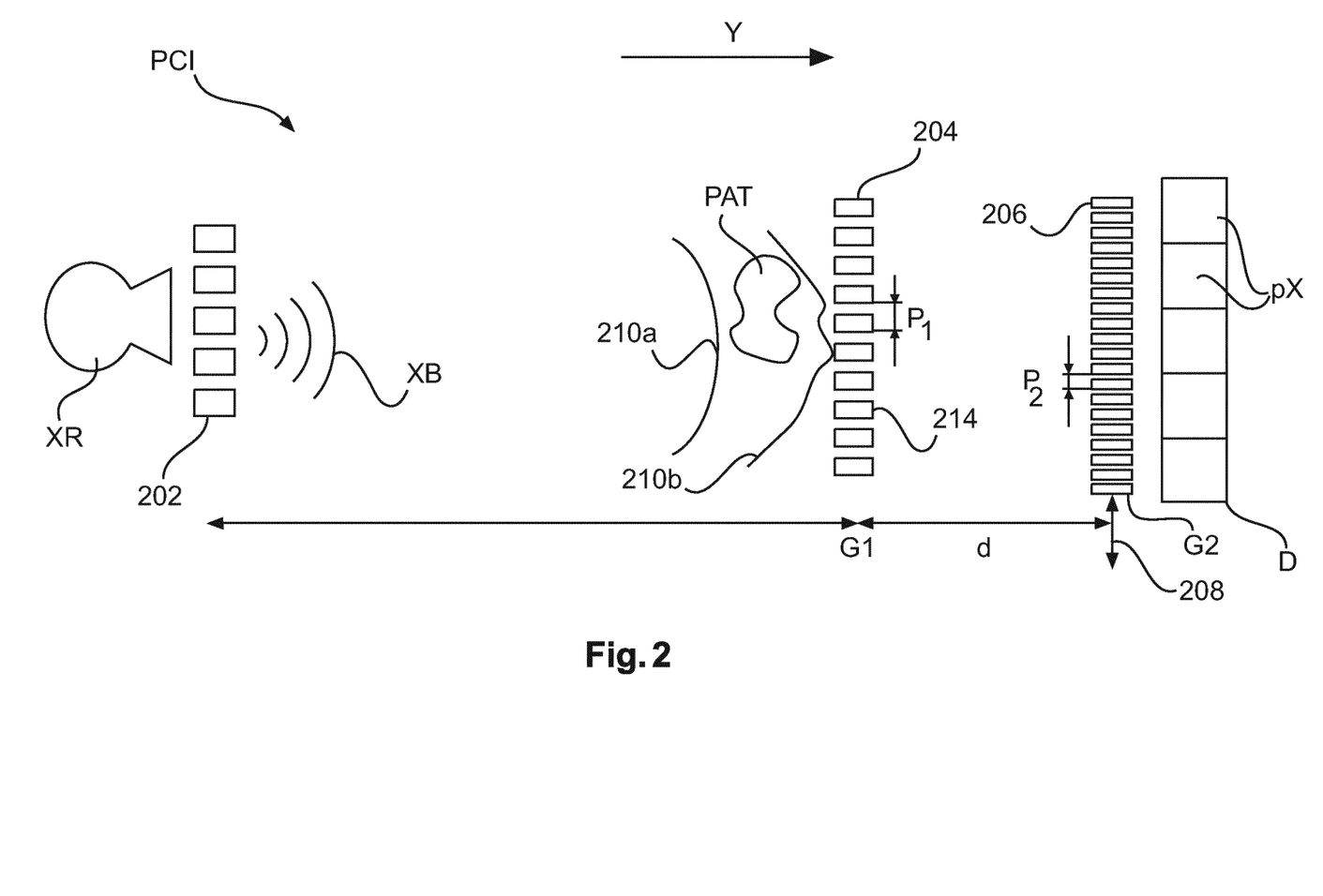
FIG. 2 shows phase contrast imaging equipment as used in the arrangement according to FIG. 1.

In FIG. 2, X-ray source XR is depicted having a source grating element 202 arranged adjacently. X-ray radiation 114 penetrating source grating element 202 may be considered to be at least partially spatially coherent. X-ray radiation XR comprises individual wave fronts of which wave front 210a is depicted as a wave front before penetration of object PAT while wave front 210b is depicted after penetration of object PAT, having an illustrated phase-shift.

Arranged after object PAT and spaced apart from both the detector element 104 and an analyzer grating $G_2$ 206 by distance d, is phase grating $G_1$ 204 having a pitch $P_1$. Detector D, with its individual detector pixel elements 116, subsequently detect an interference pattern of X-ray radiation XR, imposed by phase grating $G_1$ 204 and analyzer grating $G_2$ 206.

Actuator element 208 is schematically illustrated as being adapted to laterally displace analyzer grating $G_2$ 206 (having pitch $P_2$) relative to X-ray tube XR with source grating 202, phase grating $G_1$ 204 and X-ray detector D. However, actuator element 208 may be arranged at any of the grating elements 202, 204, 206 for displacement x. Said actuator is used to effect what is known as "phase stepping". In phase stepping, one of the source grating, the phase grating, and the analyzer grating is displaced laterally with respect to the other gratings and the X-ray detector element by a fraction of its respective grating pitch, e.g., a fourth, sixth, or eighth of the grating pitch of the respective grating element. Each of those displacements constitutes a phase stepping state. Image acquisition and lateral displacement is repeated, e.g., four, six, or eight times, on order to acquire a plurality of projection images. The plurality of projection images acquired during the phase stepping together form a phase stepping series of projection images. In other words, each detector pixel detects for each step in the phase stepping a signal (that in general depends on the position of said pixel) of varying intensity I as recorded in the phase stepping series. The plurality of intensity signals I can then be analyzed to recover attenuation data f, phase shift data g and small scatter angle data h.

More particularly, for each projection angle θ, during phase stepping of, e.g. $G_2$, the radiation signal intensity I is detected by a detector pixel px and said signal oscillates at a said detector pixel/channel px with the phase stepping x scan in approximation as follows:

$$I(x) = A\left(1 + V\cos\left(2\pi\frac{x}{P_2} + \varphi\right)\right) \quad (1)$$

where A is related to the overall linear attenuation of the ray, φ is related to the local phase shift gradient of the wave front 201b, V ("visibility") is the small angle scattering, $P_2$ is the grating pitch, and x is the relative displacement of the grids $G_1$ and $G_2$ during phase stepping.

The oscillating signal I is analyzed by signal processing circuitry SC and the values A,V, φ can be extracted from said curve. In one embodiment, signal processing circuitry implements a Fourier analyzer such as a fast fast-Fourier transform (FFT) to effect a Fourier decomposition of the respective I intensity curves as detected by the respective detector pixels px. The Fourier decomposition then yields A as the DC component, the amplitude of the frequency component $v=1/P_2$ being a measure for the visibility V and φ is the phase of the frequency component $v=1/P_2$.

It is understood herein, that the approximation as per (1) is in general different for each pixel px as each pixel px will, in general, "see" a different intensity I for each x. The Fourier analysis to recover the values A, V, φ is therefore carried out separately (sequentially or in parallel) for each pixel px.

The projection of the phase gradient ∂Φ of the wave front is related to and can be recovered from the measured phase value φ of the intensity curve I through the relation $$\varphi = \lambda\frac{d}{P_2}\partial\Phi/\partial x.$$

The variable x denotes the phase stepping direction, d the distance between gratings $G_1$ and $G_2$, and λ the wave length of the design energy $E_d$. The design energy approximates the energy spectrum of the in general polychromatic radiation. See for instance equation (1) in the paper of T. Weitkamp et al in "Optics Express", vol 13, No 16, pp 6296-6304 (2005).

Grating-based differential phase-contrast imaging may allow employing a relatively broad-banded X-ray source, e.g., with ΔE/E~10%. In other words, polychromatic X-ray radiation rather than monochromatic X-ray radiation having substantially only a single wavelength may be employed for phase-contrast imaging.

It is understood that FIG. 1 shows the arrangement of PCI in a highly schematic way as interposed between x-ray source and detector D. In one embodiment, the PCI gratings $G_1$, $G_2$ are integrated in detector D's housing, in particular are mounted in one embodiment on the detector D, and the source grating element 202 is integrated in the exit portion of x-ray source XR.

In another embodiment, the phase retrieval is not done by the phase-stepping approach where one of the gratings is moved, but it is done by the Fourier Method. This Fourier method is described in more detail by A. Momose et al in "Four-dimensional X-ray phase tomography with Talbot interferometry and white synchrotron radiation: dynamic observation of a living worm", Vol. 19, No. 9, OPTICS EXPRESS, pp 8423, April 2011.

The processing circuitry SC includes in one embodiment suitable conversion unit to convert at least the attenuation data A from the Fourier decomposition into respective line integrals. A corresponding conversion may also be performed for the other 2 channels to obtain respective sinogram data. In one embodiment, the differential data g as output by the Fourier decomposition are scaled by $$\varphi = \lambda\frac{d}{P_2}\partial\Phi/\partial x.$$

In an alternative embodiment no scaling is performed on the differential data channel and the sinogram g is made up from the data as supplied by the Fourier decomposition, that is, in this embodiment g=φ. Line integral conversion for the small scattering channel h may be done as reported by M. Bech et al in "Quantitative x-ray dark-field computed tomography", Phys. Med. Biol. 55 (2010) 5529-5539 where it is proposed to express the small angle scattering data h in terms of a linear diffusion coefficient ε (that is, the specific scattering width per unit length). See for instance expression (14) in Bech at p. 5533.

In sum, the signal processing circuitry SC processes the projection data A,V, and φ as detected by the detector D during the phase stepping SC therefore supplies, after respective line integral conversion, in general three image data sinograms f, g, h via respective channels: the attenuation data channel, the phase gradient channel and the small angle scattering channel.

The attention sinogram f records, up to beam hardening corruption, for each projection angle θ, line integrals, that is, projections of the liner attenuation coefficient along respective projection directions though the object.

The phase gradient sinogram g records for each projection angle θ, the respective projection of the phase gradient and the small scatter sinogram h records, for each projection angle θ, the respective projection of the amount of attenuation caused by the small angle scatter. Each of the differential data g and the small scattering data h are in general likewise corrupted by beam hardening.

As will be described in greater detail below, signal corrector COR receives the sinogram data f and g and/or h and corrects the projection data in some or all of the sinograms f and/or g and/or h for beam hardening corruption. The corrector COR then outputs corrected sinogram(s) and forwards the corrected sinogram(s) f̂ and/or ĝ and/or ĥ to reconstructor RECON.

Reconstructor RECON is configured to reconstruct images from the corrected sinogram, data to generate a respective type of cross-sectional image ("slice") indicative of the object under examination, for example the interior anatomy of patient PAT. The image type is either attenuation contrast or phase contrast or small angle scattering contrast, depending on which one of the three corrected sinograms are processed by the reconstructor RECON. The respective slices for each scan position z of interest can then be combined into volumetric data. Individual slices or the whole or parts of the volumetric data can then be visualized on monitor M by operation of visualizer VS or otherwise image processed and stored for later reference.

According to one embodiment, the reconstructor RECON uses filtered back-projection (FBP) but other reconstruction algorithms such as iterative reconstruction algorithms (statistical or algebraic) are also envisaged herein.

It will be appreciated that in general not all of the three sinograms are required and it will be understood that the signal processing circuitry SC may process the raw projection data selectively to only extract one or more of desired ones of the sinograms. For instance, in one embodiment it is only the phase gradient sinogram g (and not the small scatter sinogram) that is extracted and then forwarded to reconstructor RECON for reconstruction into phase contrast slice/volume. Any combination of the attenuation data channel f with either one or both of the other two sinogram channels g,h are envisaged herein and the console CON is configured with suitable selection means (which is either user or protocol responsive) to control the signal processing circuitry SC to that the reconstructor is supplied with the desired sinograms data through one or more desired channels.

To better explain operation of beam hardening corrector COR in more detail at FIG. 4 below, we briefly review on beam hardening and how beam hardening is a corrected for in conventional CT context where only attenuation contrast is considered.

To convert the X-ray transmission data into path length data, logarithms ("log") of the attenuation data are taken to effect conversion into line integrals as recorded in the attenuation sinogram f as briefly mentioned above. This log data is not directly proportional to the material path lengths mainly due to beam hardening effects. The X-ray tube XR is polychromatic, i.e. its spectrum contains low energy photons as well as photons with energy near its maximum value. In general, material in the traversed object PAT tends to absorb the low energy photons (also referred to as "soft" photons) more efficiently than high energy photons. This causes a non-linearity. In particular, the transmitted X-rays become "richer" in high energy photons and become therefore more penetrating or "harder" with in-tissue path length l, that is, as the ray progresses through the imaged object PAT. In yet other words, the mean energy $E_{mean}$ increases with in-tissue path length l and thus with the amount of traversed object material. This has the effect that even completely homogenous material would appear progressively less dense. In other words, the contributions of downstream voxels along the ray's path l are erroneously detected at the respective detector pixels px as less dense than they really are. Beam hardening, if uncorrected, may incur artifacts known as "cupping" (or others) in the reconstructed images. In the following, when reference is made to either f, g, h, this should be understood as a reference to an entry in the respective sinogram for a certain projection direction with the understanding that the following computations and explanations apply to each of the projection directions so can be applied to the whole of the sinogram entries, either in parallel or sequentially. For instance, "f" in the following refers to the attenuation line integrals for a certain projection direction and similar for g, h which now denote the entry at the corresponding projection direction. Also, the same notation (f, g, or h) is used herein for the respective channels and for the data after conversion into the respective line integrals.

An exemplary empirical method for beam hardening correction (BHC) for conventional "attenuation-only" based x-ray CT (that is, where neither phase shift of the x-ray beam nor small angle scattering is accounted for) may use the following model:

$$I = \int dE\, I_0(E) S(E) e^{-\int \mu(E,l)\,dl}$$

wherein:

I is the measured intensity of the X-rays after passage through the object PAT,
$I_0(E)$ is the incident spectrum,
$S(E)$ the spectral response of the detector, and
$\mu(E,l)$ is the spatial distribution of the linear attenuation coefficient of the object along the ray parameterized by the path l. The above modeling equation is based on energy integrating detectors, but the modeling equation (and the following observations) holds true for photon counting detectors also, with the following modifications: the spectral S(E) response is a multiple step function to model the selective nature of the counting process and I corresponds to the respective counts in the respective energy intervals. See for instance p. 4682 in E. Roessl et al in "K-edge imaging in x-ray computed tomography using multi-bin photon counting detectors", Phys. Med. Biol. 52 (2007) 4679-4696.

After line integral conversion the line integral f (which in general is beam-hardening corrupted) is computed by taken logs as:

$$f = -\log \frac{\int dE I_0(E) S(E) e^{-\int \mu(E,l) dl}}{\int dE S(E) I_0(E)}$$

All involved functions vary slowly with energy (as long as no objects with a k-edge within the x-ray spectrum are involved).

It therefore appears feasible to correct these corrupted line integrals by formulating a low-order polynomial p(.) for how the mean x-ray spectrum $E_{mean}$ of the x-ray spectrum varies after passage of the beam XR through the object. The polynomial maps the corrupted line integral to a "notional" attenuation line integral at a certain reference energy $E_{mean}$:

$$\tilde{f} = fp(E_{mean}),$$

$$E_{mean} = \frac{\int dE E I_0(E) S(E) e^{-\int \mu(E,l) dl}}{\int dE I_0(E) S(E) e^{-\int \mu(E,l) dl}}$$

Of course, $E_{mean}$ is i not in general accessible experimentally. However, since the beam XB hardens slowly and monotonically as it passes through the object PAT, the mean energy increases slowly and monotonically with increasing length l through the traversed object. Consequently, the mean energy varies slowly and monotonically with the beam hardening corrupted line integral f. Thus, it is possible to use f as a "surrogate" for the mean energy, which results in a correction of sinogram f of the form $$\tilde{f} = fq(f) \quad (2)$$

where q is, again, a low-order polynomial $$fq(f) = \sum_{k=1}^{N} a_k f^k$$

where the additional factor f is multiplied into the polynomial sum for notational convenience, where the $\alpha_k$ are calibration coefficients. It is of note that, in the attenuation-only case, in order to arrive at equation (2) we harness the fact that the mean energy $E_{mean}$ can be expressed as a function in terms of the corrupted line integral. In other words, the amount by which f experiences beam hardening still uniquely determines the mean energy $E_{mean}$. Said differently in terms of functions, the beam hardening effect can be thought to be governed a "notional" (that is, in general not known) non-linear beam hardening corruption function b that expresses the functional relationship $f=b(\hat{f}, E_{mean})$ between i) the amount $\hat{f}$ of material in the object PAT traversed by the beam at a certain projection direction and ii) the attenuation data f given a certain mean energy $E_{mean}$ of the beam. In BHC for the attenuation-only case, one wishes to estimate the amount traversed material $\hat{f}$ given a measured line integral f at a certain mean energy $E_{mean}$. The polynomial expression fp ($E_{mean}$) then is an estimate for the traversed amount of material $\hat{f}$ and fp($E_{mean}$) can be written as fq(f) owing to the existence of said unique functional relationship between f and $E_{mean}$. The product fq(f) with mean energy surrogate q(f) is therefore an approximation for the inverse $b^{-1}$ of the beam hardening corruption function b as per $\hat{f}=b^{-1}$ (f, $E_{mean}$).

The unknown calibration coefficients $\alpha_k$ are obtained by scanning an object with known absorption properties such as a phantom body using the following scheme:

Scan of a water or other suitable phantom;

Calculation of BH-corrupted line integrals as per the above:

$$f = -\log \frac{\int dE I_0(E) S(E) e^{-\int \mu(E,l) dl}}{\int dE I_0(E) S(E)};$$

Calculation of higher order sinograms from the BH-corrupted data $f_k=f^k$, k=1, . . . , N, where $f^k$ denotes pixelwise exponentiation of the actually measured sinogram data f acquired from the object PAT scan.

FBP reconstruction of each $f_k$, resulting in images $X_k$.

Least squares fit of the polynomial coefficients $\alpha_k$ to minimize the difference to the "ground truth" furnished by the known voxel date X of the water phantom:

$$\Delta^2 = \left\| X - \sum_{k=0}^{N} a_k X_k \right\|^2$$

Since FBP is a linear operator, the coefficients $\alpha_k$ can be used in subsequent scans in the projection domain as per equation (2). In other words, because the $\alpha_k$'s are known, correction function q(f) can be computed for any forthcoming sinogram f, in particular the sinograms of the patients or samples of interest. Said correction coefficients are then multiplied (pixelwise) into the given sinogram f to arrive at the beam hardening corrected sinogram $\tilde{f}=fq(f)$ for the attenuation data f Turning now to the instant case of DPCI imaging and using the intensity model for the phase stepping as per equation (1), the model of the signal generation process model is more involved as for the attenuation-only case discussed above. For DPCI the signal model is:

$$I(x) = \int dE I_0(E) S(E) e^{-\int \mu(E,l) dl} + \int dE V(E) I_0(E) S(E) e^{-\int \mu(E,l) dl} \cos\left(2\pi \frac{x}{P_2} + \phi(E_d) \frac{E_d}{E}\right)$$

where the measured intensity I now depends additionally on i) the visibility of the interference pattern V(E), ii) the relative grating position x (as applied during the phase stepping as described above with reference to FIG. 2) and iii) on the phase deflection φ caused by object PAT.

More particularly, in the DPCI signal model:

E is the energy;

l is the in-tissue path length through object PAT;

I is the intensity recorded at grid position x in the imaging run, whereas $I_0$ is the incident "reference" intensity which is known or can be recorded at the pixels in an "air" or blank scan;

V is the visibility, that is, the modulation depth of the interference pattern.

$E_d$ is the design (or more generally speaking a reference) energy. This is the energy at which the interferometer of FIG. 2 responds with the best visibility V. In other words, the design energy is the energy where the observed modulation depth of the interference pattern is at its maximum. This modulation depth may be probed during the blank scan and is quantified by the fitted value V to the data acquired during the blank scan;

x=grid position;

φ=phase shift of an interference pattern caused by object PAT and as recorded at the detector via the interferometric arrangement as per FIG. 2—the phase shift gradient ΔΦ of the wave is recoverable therefrom as mentioned above in relation to the Weitkamp paper.

As mentioned earlier with reference to FIG. 2, in one embodiment of DPCI the beam-hardening corrupted differential line integrals g are retrieved by fitting the model function $I(x) \approx I_0(1+V \cos(2\pi x/P_2+g))$ to the phase stepping series. Since the data g is "differential" (that is, g encodes the gradient of the X-ray wave's phase shift), the above outlined scheme for BHC for the attenuation case does not appear to be applicable here. In particular, the very same phase gradient for an object can result in different measured beam-hardening corrupted data g. Consequently, the beam-hardening corrupted phase gradient data g cannot be used in itself as a surrogate for the mean energy as has been done before for the attenuation data f.

Figure 3:
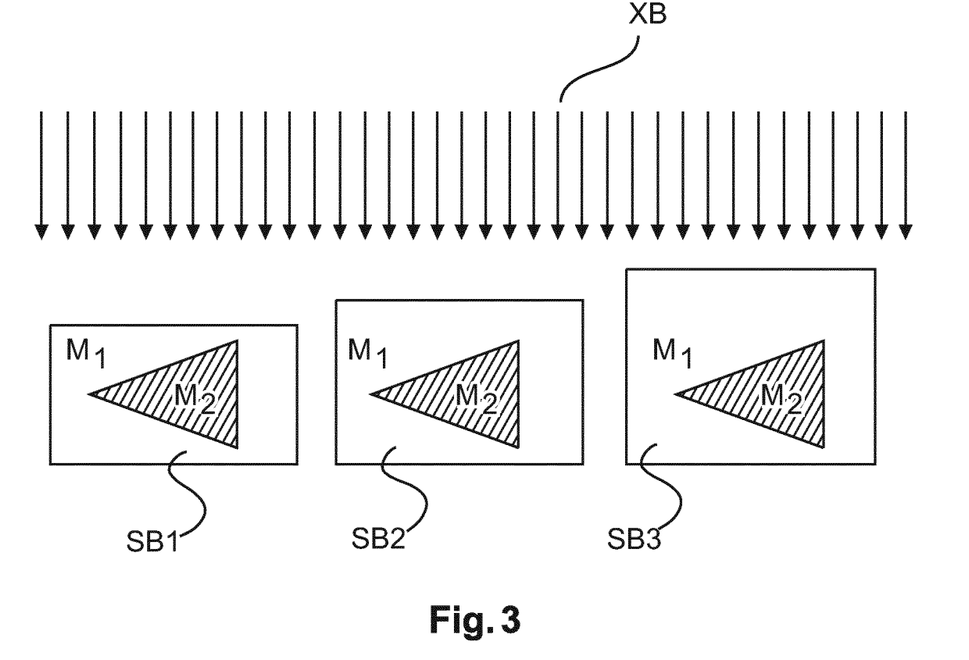
FIG. 3 schematically shows beam hardening corruption of differential data.

FIG. 3 illustrates schematically the beam-hardening corruption of differential data. There are shown three sample bodies $SB_{1-3}$. The x-ray beam XB is assumed to pass through each of them. Each sample body incorporates a prism part $M_2$. The prism part represents an inhomogeneity, that is, each prism portion is assumed to have a different density than a surrounding homogenous background material $M_1$. Each of the respective prism portions $M_2$ causes a phase shift of the x-ray beam XB (when looked at as a wave) and hence causes a corresponding amount of deflection of the X-ray beam XB. The beam's XB deflection is the same for all three sample bodies $SB_{1-3}$. However, the rightmost sample body $SB_3$ will cause most beam hardening since its background material $M_1$ is "thicker" in propagation direction than the background materials $M_1$ in the other two sample bodies $SB_{1,2}$. Thus, the mean energy $E_{mean}$ will be higher for sample body $SB_3$ than for the other two sample bodies $SB_{1,2}$ which in turn results in a smaller measured phase gradient for $SB_3$ than it does for the other two sample bodies $SB_{1,2}$. In other words, the same "true" (that is, non-beam-hardening corrupted) phase gradient line integral ĝ is mapped by the measurement onto different values of g, making an inversion from g back to ĝ impossible.

It is therefore proposed herein to correct the phase gradient data g by a correction factor that is computed not from the phase gradient data g but is computed instead from the attenuation data f More particularly, like in the attenuation contrast case, a low-order polynomial model is used for the correction as per $\tilde{g}=g\hat{p}(E_{mean})$ which is reasonable since the phase gradient changes slowly with the mean energy. But now the analogy as per the preciously discussed attenuation case is abandoned because rather than expressing $E_{mean}$ in terms of g, we again propose to express $E_{mean}$ in terms off and use this to arrive at the correction factor for the phase gradient line integral g. In other words, we again, use the fact that the beam-hardening corrupted attenuation contrast line integral $$f=-\log(\bar{I}/I_0)$$

varies slowly and monotonically with the mean energy $E_{mean}$, but this time we use a polynomial function q̂ of the attenuation contrast line integral f as a surrogate for the mean energy for the phase gradient line integrals g. This ansatz results in the proposed model $$\tilde{g}=g\hat{q}(f) \qquad (3)$$

for the phase gradient line integral correction and gq̂(f) is now the estimate for the inverse beam correction function with q̂(f) the correction factor computed only from the attenuation data. So, although now dealing with the BH correction for differential line integrals g, the mean energy surrogate q̂ is still expressed in terms of the attenuation line integrals f and not in terms of g because g does not uniquely determine $E_{mean}$.

Figure 4:
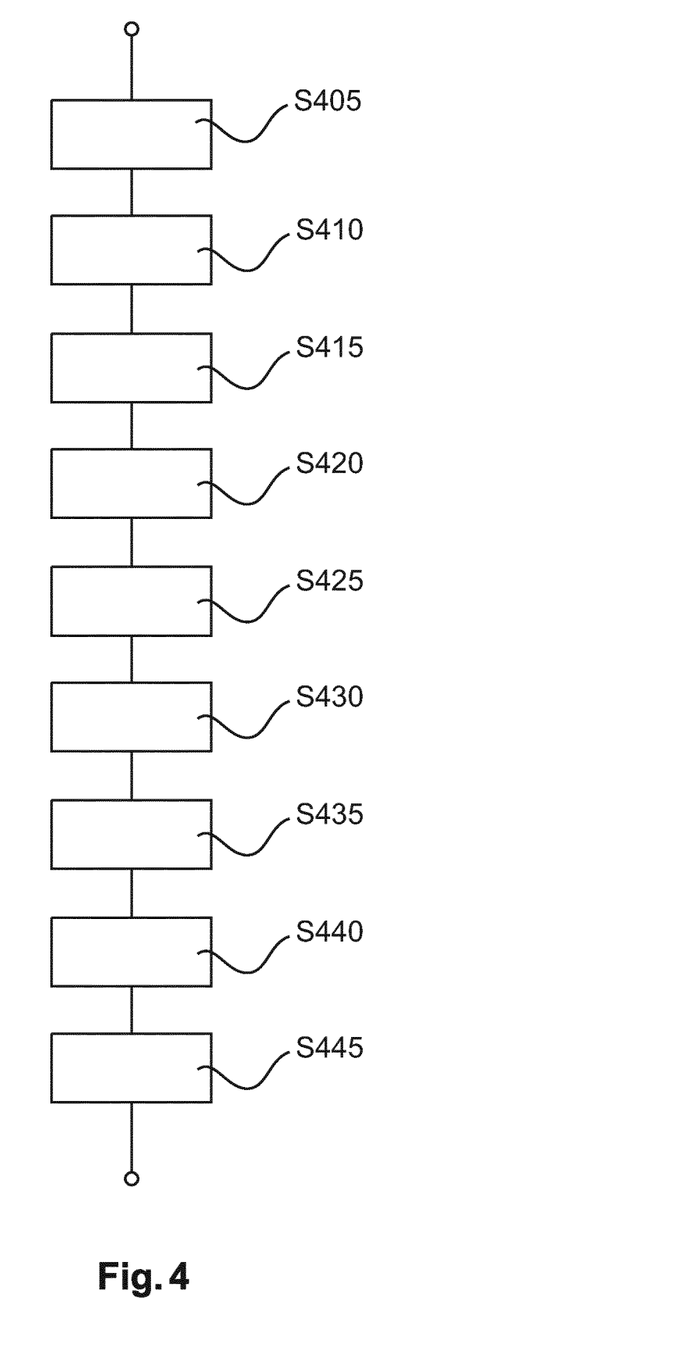
FIG. 4 shows a flow chart for a beam hardening correction method.

Reference is now made to the flow chart in FIG. 4, where steps of a beam hardening correction method are shown that underlie operation of the proposed corrector COR. The method allows correcting a given differential phase shift sinogram g and/or a given small angle scattering sinogram h for beam hardening. The method includes a calibration phase and a correction phase.

Turning now first to the calibration phase:

At step S405, a phantom body PB is scanned by using a CT scanner IMA to acquire projection raw data of the phantom PB. In one embodiment, the phantom body incorporates a sufficient number of density inhomogeneities as will be explained in more detail below at FIG. 5. It has been observed that the present method yields good results if non-truncated projections are used. Preferably, it is therefore ensured that the phantom body fits completely into the reconstruction field of view of the scanner CT.

At step S410, based on the projection raw data, BH-corrupted differential line integrals g and/or the BH corrupted small angel scattering line integrals h and/or the attenuation line integrals f are computed.

In one embodiment, this is done by fitting the model $I(x) \approx I_0(1+V \cos(2\pi x/P_2+g))$ to the phase stepping data series as has been explained above in connection with FIG. 2.

In one embodiment, the computation of the BH-corrupted attenuation line integral includes a conversion as per $f=-\log(\bar{I}/I_0)$.

At step S415, higher order "mixed" sinograms are computed from the BH-corrupted data f and the phase gradient line integrals g according to $g_k=gf^k$, k=0, . . . , N. In other words, the attenuation sinograms f is raised pixelwise to any one of the required powers k=0 through N and is then multiplied pixelwise into sinogram g to effect the mixing. In other words, and very much counterintuitively, it is proposed herein to mix (for terms k>0) data from the phase contrast channel with data from the attenuation contrast channel.

At step S420, each of the mixed sinograms $g_k$ is reconstructed by reconstructor RECON into images $Y_k$, that is, the mixed sinograms $g_k$ are mapped from projection domain into image domain. In one embodiment, FBP reconstruction is used but other linear reconstruction methods such as algebraic iterative reconstruction method or BPF (back-projection-filtration) methods are also envisaged.

At step S425 the polynomial coefficients $b_k$ are determined for surrogate polynomial q̂. In one embodiment a least-squares-fit of polynomial coefficients $b_k$ is computed to minimize the difference to the known ground truth voxel data Y of phantom PB:

$$\Delta^2 = \left\| Y - \sum_{k=0}^{N} b_k Y_k \right\|^2$$

Step S425 can be carried out by a curve fitting module CF that is run in one embodiment by the image processor IP. The coefficients bk parameterize the approximation polynomial q̂(•) which is therefore known once the coefficients bk are computed. Note, that the correction polynomial q̂(•) has a zero order term (k=0) in DPCI, but not so in the attenuation contrast case (where k≥1). The coefficients bk can be stored in a look-up table or other suitable data structure for later reference when needed in the correction phase. Steps S410-S425 can be performed by a calibration module CAL integrated in image processor IP. In an alternative embodiment, the calibration module CAL is located at a different image processor.

In the following, method steps of the correction phase are described.

At step S430, the object PAT of interest (which is different from the phantom body PB) is scanned by the scanner IMA or by a different scanner to obtain projection raw data of the object PAT.

In step S435, the projection raw data acquired from the object PAT is processed into i) attenuation data f and ii) into at least one of phase gradient data g and small angle scattering data h. This can be done similar to step S410. For instance, the object PAT projection data can be processed by the signal processing circuitry SC used in the phase retrieval operation as explained earlier in connection with FIG. 2.

In step S440, the correction factor is then computed as per equation (3) by applying the approximating polynomial q̂(f) to the given attenuation data f.

In step S445, the correction factor q̂(f) is then combined with the phase gradient data g. In one embodiment this is done by applying the correction factor q̂(f) to the given phase gradient data g by pixelwise multiplication with g to obtain the BH corrected phase gradient data g̃. As previously with the attenuation-only case, we harness the fact that FBP is a linear operator which allows us to apply the correction factor q̂(f) in the projection domain although the coefficients $b_k$ have been computed in the image domain as per step S425. It has been observed by Applicant that the correction factor q̂(f) can also be used in any linear iterative reconstruction algorithms—this being true despite the fact that the calibration procedure explicitly uses the linearity of the FBP reconstruction algorithm. Steps S440-S445 are performed by a corrector module COR.

In an optional follow-up step, the corrected phase gradient data g̃ is then reconstructed by reconstructor RECON to obtain a phase contrast slice image. The steps S440-S445 are then repeated for each sinogram g for any desired z position to obtain a plurality of corrected sinograms which may then be reconstructed and combined into a phase contrast volume.

As mentioned earlier, DPCI also provides a third data channel, namely the dark-field or small angle scattering signal h, which is derived from the fitted visibility variable V. This signal can also be used for tomographic reconstruction and has been found to likewise suffer from beam-hardening artifacts. One reason for this is that the visibility of fringes behind the interferometer PCI depends on energy.

The same procedure as described above in relation to the differential phase contrast channel g can be applied mutatis mutandis and instead of or in addition to the small angle scattering signal h in order to correct for beam-hardening artifacts. For instance, in step S420, mixed terms hf are then formed.

The above steps S405-S445 may not necessarily be carried out in the order as exemplary shown in the flowchart of FIG. 4. In particular the scanning of the phantom at step S405 and the scanning of the actual object PAT to be imaged at S430 may be carried out in any desired order.

Also, the method as proposed herein is applicable not only to axial scans but to any type of scans, including parallel, cone and helical scans. More particularly, "sinogram" as used herein is to be construed broadly, that is, the line integrals entries in the sinograms f, g, h for the respective projections may be 1-dimensinal but may also be 2-dimensional depending on the number or detector pixel rows used for the scan, for instance, in parallel or cone scans, the sinogram entries are 2D.

Also, the polynomial coefficients $b_k$ computed in the calibration phase for the sinograms at a certain scan position z are usable to correct scan data at other z positions. Also, the scan technique used to acquire the phantom scans in step S405 may be different from the scan technique used for the actual object scan at step S430. For instance, the phantom may be scanned axially whereas the object is scanned helically. Specifically, the coefficients $b_k$ (and hence the polynomial q̂(•) computed from the axial scan data f,g,h can still be used to correct the helical scan sinograms as per step S440-S445.

Figure 5:
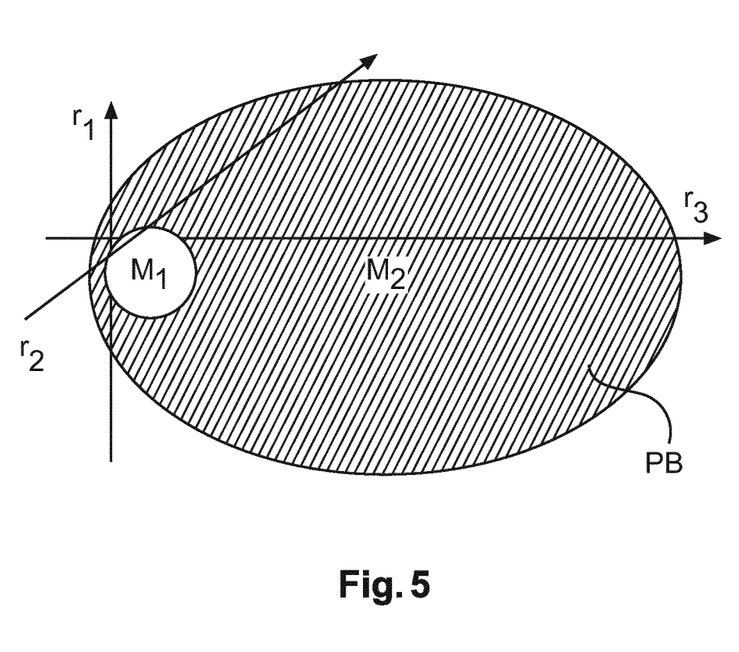
FIG. 5 shows a schematic representation of cross section across a phantom body.

Referring now to FIG. 5, there is shown a cross section through an exemplary embodiment of the phantom body for use in the calibration phase, in particular in calibration step S405. The density distribution of the phantom body PB allows sampling different combinations of phase gradients and attenuations. In particular, it is ensured that rays travelling along relatively long in-tissue path lengths through the object (thus incurring greater amount of beam-hardening corruption) will also experience deflection. This makes the calibration procedure more stable.

FIG. 5 shows one embodiment of a DPCI BHC calibration phantom geometry as envisaged herein. In one embodiment, the phantom body PB has an elliptic cross section. The body PB incorporates one or more enclosures or insets $M_1$ that are formed from a material having a less density than the density of the surrounding background material $M_2$.

In one embodiment the background material $M_2$ is formed from water or PE whereas the low-density inserts $M_1$ are defined by air enclosures or cavities.

As can be seen in FIG. 5, the insert $M_1$ is positioned on the major axis of the ellipse in order to ensure that rays travelling along the longest path $r_1$ through the phantom PB experience deflection. By having the low-density insert $M_1$ arranged at a terminal portion to either side of the major axis, it is furthermore ensured that rays with different path $(r_2, r_3)$ lengths through the background material $M_2$ likewise experience deflection caused by the intervening low density insert $M_1$.

Although an embodiment with a single insert $M_1$ is also envisaged herein, the phantom body PB preferably incorporates a plurality of low density inserts or cavities $M_1$. Having a phantom body with plurality of such inserts/cavities allows increasing the number of rays that will experience sufficiently large deflections which, in turn, result in a more stable calibration. This is because large deflections will cause the image data to include high contrast information which then afford a more stable fit when computing the polynomial coefficients $b_k$. Therefore in one embodiment, the phantom body has a spongy or foamy structure. The phantom body may be manufactured to have a relatively rigid consistency but soft, more jelly-like consistencies are likewise envisaged.

It will be understood from the above that the elliptic cross section is but one embodiment which however is particularly suitable in a medical context because such a geometry corresponds well with cross sections across the human torso. However other areas of application might call for different geometries such as in baggage scanning or nondestructive material testing.

Although the components reconstructor RECON, corrector module COR and calibrator module CAL are shown in FIG. 1 as integrated into a single image processor IP, this is but one embodiment and a at least partly distributed architecture is likewise envisaged herein where one or more of the components are located remotely and are connected with each other and/or with the image processor IP in a suitable communication network.

In one embodiment, image processor IP (or at least some of the components) is arranged as a dedicated FPGA or as hardwired standalone chip.

In an alternate embodiment, image processor IP and some or all of its components are resident in work station CON running as software routines thereon. Image processer IP and its components may be programmed in a suitable scientific computing platform such as Matlab® and may be translated into C++ or C routines maintained in a library and linked when called on by work station CON's operating system.

Although in the above, a grating based setup has been described to extract the phase shift contribution from the measured projection data, other PCI (phase contrast imaging) principles may likewise be used, such as analyzer-based imaging or Propagation-based imaging.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with, or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:
1. A beam hardening correction method, comprising:
   acquiring interferometric tomographic image data by exposing an object to an x-ray beam emitted by an x-ray source of an imaging apparatus and after passage of the x-ray beam through the object, the acquired interferometric tomographic image data including attenuation data and at least one of phase gradient data and small angle scattering data; and
   combining at least one respective correction value with the phase gradient data or with the small angle scattering data, wherein the respective correction value is computed by applying a function to the attenuation data, the function being configured to model an increase of a mean energy of the x-ray beam as the x-ray beam passes through the object.

2. The beam hardening correction method of claim 1, wherein the function is a polynomial.

3. The beam hardening correction method of claim 1, further comprising:
acquiring tomographic calibration image data of a phantom body by using the x-ray source;
determining one or more coefficients of the function by fitting the tomographic calibration image data to predetermined reference image data, wherein the one or more coefficients parameterize said function.

4. The beam hardening correction method of claim 1, wherein the imaging apparatus is a computed tomography scanner configured to acquire at least the phase gradient data and/or the small angle scattering data.

5. The beam hardening correction method of claim 2, wherein a degree of the polynomial is between 2 and 6.

6. The beam hardening correction method of claim 3, wherein the fitting is based on a least squares method.

7. The beam hardening correction method of claim 3, wherein the phantom body is formed from a material that incorporates at least one discrete portion having a density different from a density of a surrounding phantom body material.

8. The beam hardening correction method of claim 7, wherein the discrete portion is defined by an air-filled cavity.

9. A non-transitory computer readable medium encoded with computer readable instructions, which, when executed by a processor, cause the processor to perform a beam hardening correction method, the method comprising:
acquiring tomographic image data by exposing an object to an x-ray beam emitted by an x-ray source of an imaging apparatus and after passage of the x-ray beam through the object, the tomographic image data including attenuation data and at least one of phase gradient data and small angle scattering data; and
combining at least one respective correction value with the phase gradient data or with the small angle scattering data, wherein the respective correction value is computed by applying a function to the attenuation data, the function being configured to model an increase of a mean energy of the x-ray beam as the x-ray beam passes through the object.

10. The non-transitory computer readable storage medium of claim 9, wherein the function is a polynomial.

11. The non-transitory computer readable storage medium of claim 9, further comprising:
acquiring tomographic calibration image data of a phantom body by using the x-ray source; and
determining one or more coefficients of the function by fitting the tomographic calibration image data to predetermined reference image data of the phantom body, wherein the one or more coefficients parameterize said function.

12. The non-transitory computer readable storage medium of claim 10, wherein a degree of the polynomial is between 2 and 6.

13. The non-transitory computer readable storage medium of claim 11, wherein the fitting is based on a least squares method.

14. The non-transitory computer readable storage medium of claim 11, wherein the phantom body is formed from a material that incorporates at least one discrete portion having a density different from a density of a surrounding phantom body material.

15. The non-transitory computer readable storage medium of claim 14, wherein the discrete portion is defined by an air-filled cavity.

16. The non-transitory computer readable storage medium of claim 15, wherein the imaging apparatus is a computed tomography scanner configured to acquire at least the phase gradient data and/or the small angle scattering data.

17. An imaging device for performing a beam hardening correction, comprising:
a digital storage memory configured to store processor executable instructions; and
a processor configured to execute the processor executable instructions to:
acquire interferometric tomographic image data by exposing an object to an x-ray beam emitted by an x-ray source of the imaging device and after passage of the x-ray beam through the object, the acquired interferometric tomographic image data including attenuation data and at least one of phase gradient data and small angle scattering data; and
combine at least one respective correction value with the phase gradient data or with the small angle scattering data, wherein the respective correction value is computed by applying a function to the attenuation data, the function being configured to model an increase of a mean energy of the x-ray beam as the x-ray beam passes through the object.

* * * * *